United States Patent [19]
Lawhorne et al.

[11] Patent Number: 5,546,603
[45] Date of Patent: Aug. 20, 1996

[54] HEADBAND WITH PONYTAIL-RECEIVING FEATURE

[75] Inventors: Charles S. Lawhorne; Kerry B. Lawhorne; Laura M. Helyer, all of Casselberry, Fla.

[73] Assignee: Athletic Images, Inc., Casselberry, Fla.

[21] Appl. No.: 241,642

[22] Filed: May 12, 1994

[51] Int. Cl.$^6$ ........................................................ A42C 5/02
[52] U.S. Cl. .............. 2/181; 2/171; 2/207; 2/DIG. 11; 87/13
[58] Field of Search .................. 2/171, 174, 181, 2/181.2, 181.4, 181.6, 200.1, 209.3, 209.7, 207, 311, 338, DIG. 11; 63/3, 4; 87/8, 9, 13; 132/275

[56] References Cited

U.S. PATENT DOCUMENTS 4,723,325  2/1988  Perry ............................................. 3/207
4,998,544  3/1991  Oberfell ...................................... 132/212

*Primary Examiner*—Diana Biefeld
*Attorney, Agent, or Firm*—Gerald E. Linden

[57] ABSTRACT

Various embodiments of a headband are described, each having a ponytail receiving feature. In some of the embodiments, the ponytail-receiving feature is a separate and distinct ring-like element. In other embodiments, the ponytail-receiving feature is an opening created in the headband itself. The headband may be formed of one or more braided strands. A four-strand braid may have two groups of two strands each, at a ponytail-receiving location, to form the ponytail-receiving feature. In an embodiment, one long strand may be braided back onto itself, its two ends forming loops for defining the extremities of an integral ponytail-receiving feature. In a preferred embodiment, a relatively long strand and a relatively short strand are braided to form a headband with integral ponytail-receiving feature. An optional visor element is also described.

6 Claims, 7 Drawing Sheets

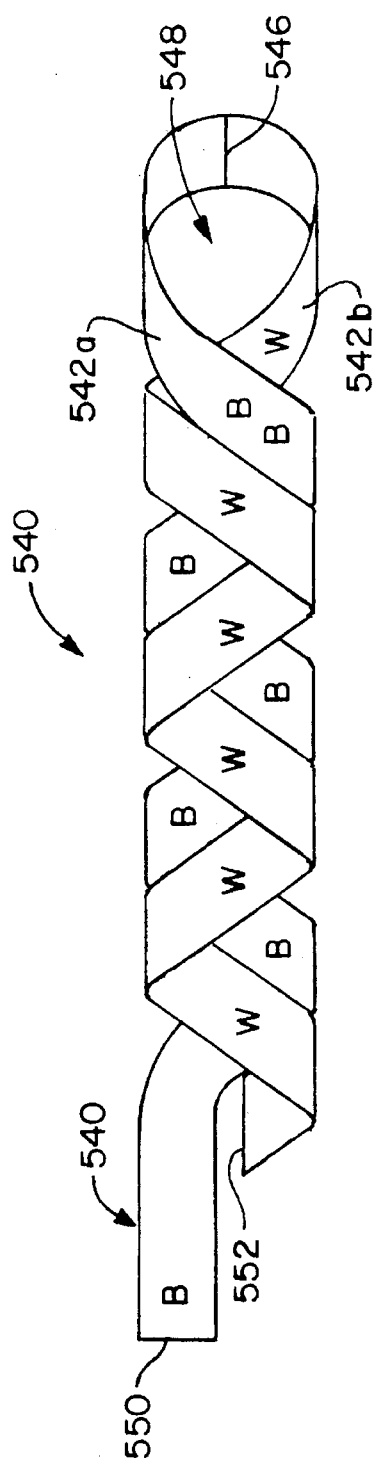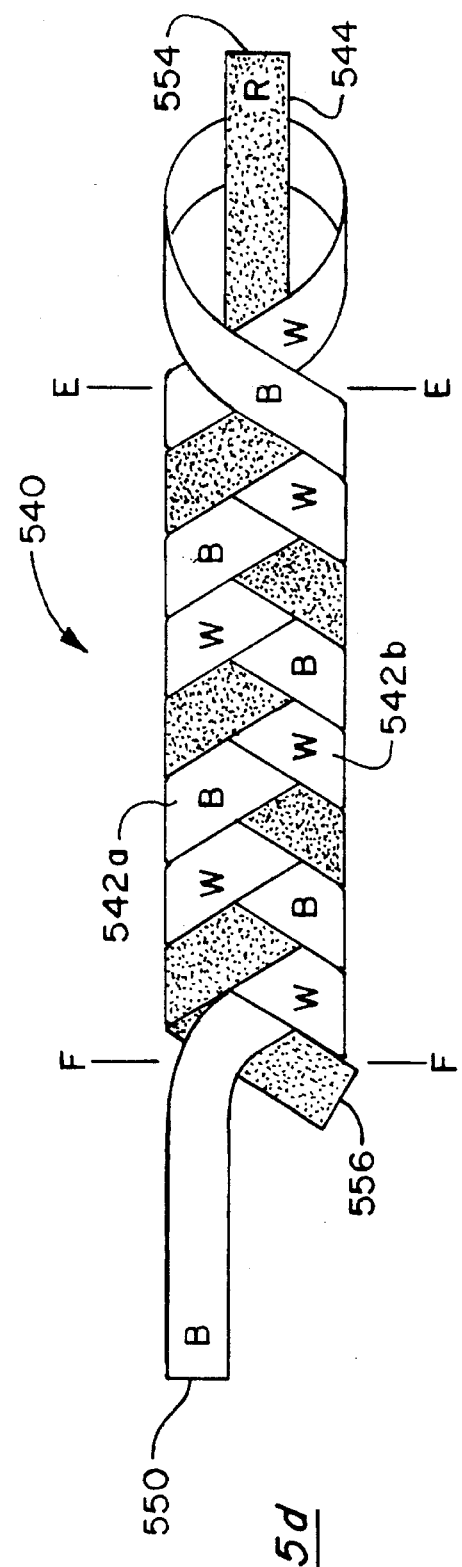
FIG. 5c
FIG. 5d

HEADBAND WITH PONYTAIL-RECEIVING FEATURE

TECHNICAL FIELD OF THE INVENTION

The invention relates to apparel worn about a person's head, for example, for absorbing perspiration and for holding hair in place.

BACKGROUND OF THE INVENTION

Headbands are worn by people for both utilitarian and non-utilitarian (e.g., fashion) purposes. For purposes of this discussion, the utilitarian purposes of headbands will be discussed.

Headbands are often worn by a person engaging in athletics (e.g., while playing tennis) for the purpose of absorbing perspiration from the person's forehead (in this case, a headband is also referred to as a sweatband), for keeping hair from impairing the person's vision, etc.. Generally, a headband is a flat strip of material worn around a person's head, encircling the person's head at a position (e.g., approximately midway) between the eyes and the hairline. This can present a bit of a problem for a person having a ponytail, as to whether to position the headband above the ponytail, or below the ponytail.

U.S. Pat. No. 4,998,544 (Obergfell, 1991) discloses a combination headband and ponytail holder. The ponytail holder is generally an elongated cylinder attached to the headband, and its aperture (opening) is aligned with an aperture of the headband. FIGS. 5 and 6 of the patent would seem to provide the best views of the apparatus, and there is discussion in the text of the ends of the headband forming the aperture which is aligned with the aperture of the ponytail holder. The ends of the headband are disposed within the "cylinder" of the ponytail holder, and are stitched to the inside of the ponytail holder.

U.S. Pat. No. 4,723,325 (Perry; 1988) discloses a continuous loop, twisted into two loops, one larger than the other.

Generally, such headbands of the prior art suffer from the limitation that they must be made from an inherently elastic material in order to be fittable about a range of head sizes, and to resiliently maintain themselves in position on a person's head, among other limitations that can be found in their construction.

Another problem confronting people engaging in sports, notably out-of-doors sports (such as tennis), is shielding their eyes from the sun.

In order to cope with the sun problem, many athletes will wear caps having a bill visor, such as a typical baseball cap. However, such caps are not capable of holding a substantial amount of perspiration, are not capable of being wrung out (in contrast to a typical headband), tend to deteriorate rapidly from use, and are not amenable to machine washing (in contrast to a typical headband). Plastic sun visors that partially encircle a person's head are also known, but being totally non-absorbent of perspiration, are typically only worn for non-athletic purposes (such as for taking a stroll on a sunny day).

What is needed is an apparatus that addresses each of the above-mentioned concerns in an improved manner, and that is capable of addressing various combinations of these concerns.

DISCLOSURE OF THE INVENTION

It is therefore an object of the present invention to provide an improved headband.

It is another object of the present invention to provide an improved headband with a ponytail-receiving feature.

It is another object of the present invention to provide an improved combination of headband and sun visor.

According to the invention, a ponytail-receiving feature is incorporated into the construction of a headband.

In one embodiment the headband is a flat strip, and the ends of the strip are looped back onto the body of the headband. A ponytail-receiving ring is retained by the two loops formed at the ends of the headband. The ponytail-receiving ring may be free to rotate within the two loops, or may be secured thereto.

In various embodiments of the invention, the headband is formed as a braid, from one-or more strands. In some of these embodiments, the ponytail-receiving feature is integrally formed with the strands.

In one embodiment of a braided headband with integral ponytail-receiving feature, approximately one-third of a long strand is doubled back onto a remaining third of the strand and twisted to initiate a partial braid. The free one-third of the strand is braided into the twisted two thirds of the strand. The two free ends of the strand are looped back onto the body of the headband, and ring-forming portions of the strand pass through the loops formed thereby to define the ponytail-receiving feature.

In another embodiment of a braided headband with integral ponytail-receiving feature, a one strand is doubled back onto itself and twisted to initiate a partial braid. The midsection of this strand will become the ponytail-receiving ring. An end of this long strand forms one of the loops for the ponytail-receiving ring. Another, shorter strand is braided through the twisted (doubled, longer) strand. One end of this shorter strand forms an other of the loops for the ponytail-receiving ring.

According to a feature of the invention, the headband, including individual strands of the braids, may be formed of a folded-over strip of material, having two-or more folds.

According to a feature of the invention, the folded-over strip can be formed into a tube, and may be turned inside-out, and may have an elastic strip inserted into the tube.

According to a feature of the invention, a visor element can be attached to the headband.

Other objects, features and advantages of the invention will become apparent in light of the following description thereof.

BRIEF DESCRIPTION OF THE DRAWINGS

FIGS. 5c and 5d show, schematically, the construction of a braided headband with integral ponytail-receiving ring, according to an alternate, preferred embodiment of the invention.

DETAILED DISCLOSURE OF THE INVENTION

The invention is shown in various embodiments, the first of which is a "basic", simplified embodiment Generally, the headband of the present invention comprises a headband component (element) for partially encircling a person's head, and a ponytail ring component (element) for receiving a person's ponytail, and optionally a visor component (element) for shielding a person's eyes from the sun.

BASIC EMBODIMENTS

Figure 1:
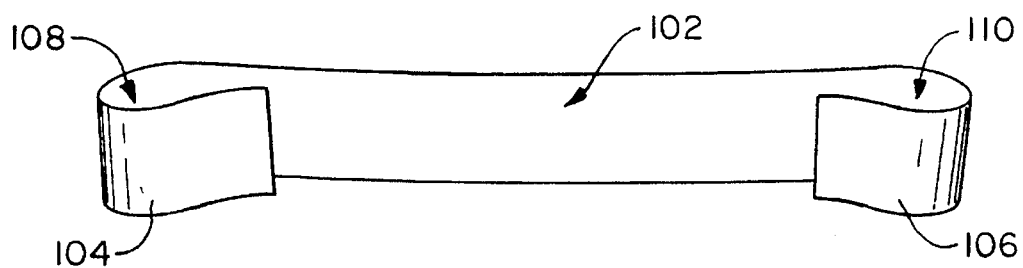
FIG. 1 is a perspective view of a flat headband component of the present invention, formed of a strip of material.

FIG. 1 shows a basic embodiment of a headband element 100 the present invention. A flat strip (band) of material 102 has two free ends 104 and 106. Each of the ends is folded back (towards the other end) upon the strip, preferably in the same direction as one another (as shown), and is fastened (such as by stitching or sewing, indicated by the "x" symbols on the drawing) to the strip, so as to form a loop 108, 110 at each of the free ends 104, 106 of the band 102.

The band 102 is preferably 1–2 inches in width (top-to-bottom, as viewed in FIG. 1), and is sufficiently long to nearly (but not quite entirely) encircle a person's head.

The band 102 is formed of any suitable material, such as cloth, cotton cloth, terrycloth, knit yarn, wool, polyester, blends of cotton and polyester, chamois, suede, or the like, and is preferably highly absorbent of perspiration.

Figure 1A:
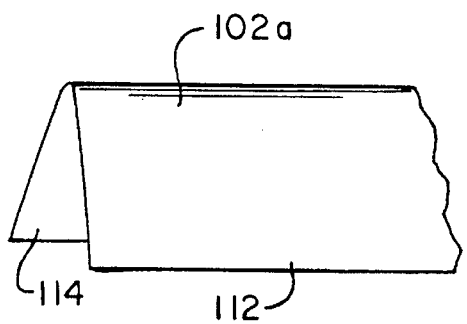
FIG. 1a is a perspective, partial view of a headband or strand component of the present invention, made of a folded piece of material.

The band 102 may be fabricated as a folded piece of material (e.g., cloth) which is initially twice as wide (2–4 inches wide) as the finished product. This is illustrated in FIG. 1a, showing the band 102a as a folded piece of material, prior to looping back the ends thereof (not shown, see FIG. 1). The folded material has two edges 112, 114, which are aligned with one another. Generally, such a folded-over piece of material will tend to remain folded over, and will be double the thickness of the material itself.

Figure 1B:
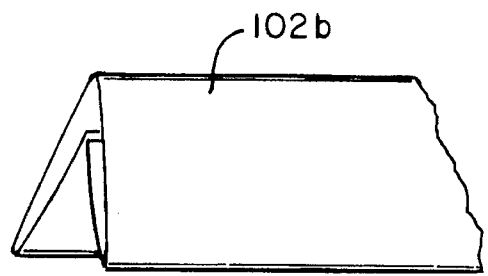
FIG. 1b is a perspective, partial view of a headband or strand component of the present invention, made of a multi-folded piece of material.

FIG. 1b illustrates that a piece of material can be multi-folded (more than one fold). The band 102b may be fabricated as a folded piece of material (e.g., cloth) which is initially up to four times as wide (4–8 inches wide) as the finished product. This is illustrated in FIG. 1b, showing the band 102b as a folded piece of material, prior to looping back the ends thereof (not shown, see FIG. 1). Generally, such a folded-over piece of material will tend to remain folded over, and in this case will exhibit four times the thickness and perspiration-absorptivity of a single thickness band.

Figure 1C:
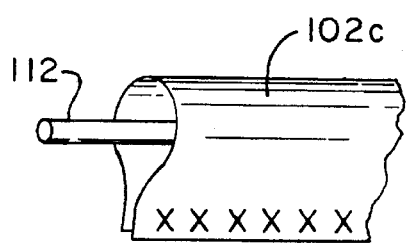
FIG. 1c is a perspective, partial view of a headband or strand component of the present invention, made of a folded piece of material, similar to the component shown in FIG. 1a, but stitched to form a tube and having an elastic strip extending through the stitched tube.

FIG. 1c illustrates that the aligned edges of the folded-over material of the band 102c (similar to 102a) can be stitched (symbols "x"), so that the band is in the form of an elongated tube. In FIG. 1c, the fold is shown as being "softer" (less creased) than in FIG. 1a.

Throughout the description, stitching is considered to be one of various conceivable "means for securing" such as for securing the aligned edges of the folded material (see FIG. 1b) to one another.

FIG. 1c also illustrates that an elastic strip 112 can be disposed within the tube of the band, and would suitably be held in place by stitching ("x") at the ends of the tube (not shown).

Figure 1D:
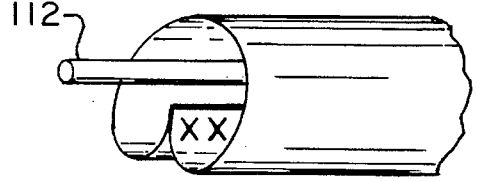
FIG. 1d is a perspective, partial view of a headband or strand component of the present invention, made of a folded piece of material, similar to the component shown in FIG. 1b, but turned inside-out prior to inserting the elastic strip.

FIG. 1d illustrates how a stitched tube (similar to the tube 102c) can be turned inside out, prior to inserting the elastic strip 112, so that the stitched seam is on the inside of the tube.

To secure the aligned edges of either the folded-over headband element, or the folded-over individual strands (described below), the headband element (or individual strand) can be sewn ("seamed") "outside out" (as in FIG. 1c), then turned "outside in", so that the unfinished ("raw") edge is on the inside of the resulting elongated tube ("tubing"), as indicated in FIG. 1d.

As will become evident, the folded component of FIG. 1a, and the tubular components of FIGS. 1b and 1c, are useful not only as headband components, but also as individual strands in a braided construction of the headband component, described hereinbelow (see, e.g., FIGS. 3, 3a, 3b, 4, 4a, 5, 5a, 5b, 5c, 5d).

Figure 1E:
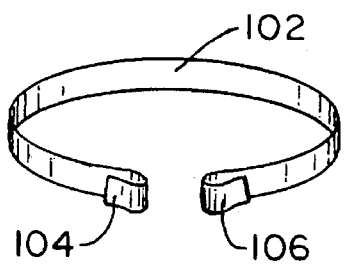
FIG. 1e is a perspective view of the flat headband component of the present invention, similar to FIG. 1, but formed into an arc for partially encircling a person's head.

FIG. 1e illustrates how the ends (e.g, 104, 106) of the band (e.g., 102) can be brought nearly together so that the band forms a curve (e.g., a circle or an ellipse)—namely, a segment of a circle (the headband element does not form a complete circle, since its ends do not touch one another). A ponytail-receiving ring is intended to be disposed in the gap between the two free ends (104, 106) of the headband component.

Figure 2:
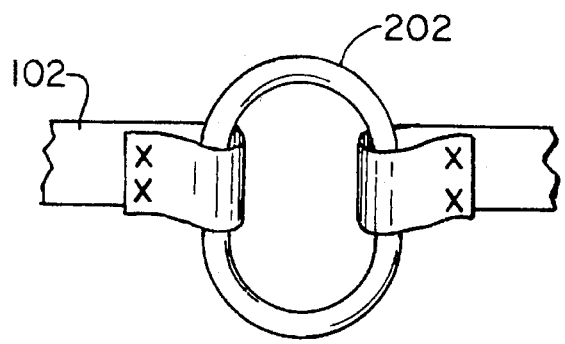
FIG. 2 is a partial perspective view of a rear portion of a headband component, in conjunction with a ponytail ring component, according to the present invention.

FIG. 2 illustrates the headband element 102 of FIG. 1e, with the addition of a ponytail-receiving element 202. Generally, the ponytail-receiving element forms a ring which is intended to receive the ponytail of a person (through the ring), as well as to "connect" the two free ends (e.g., 104, 106) of the headband component.

The ponytail-receiving element 202, or ponytail ring, can be formed of any suitable material, and is preferably resilient to allow the ring 202 to be stretched to receive a person's ponytail therethrough. To this end, the ponytail ring 202 can simply be a rubber or elastomeric ring. Or, it can be made of cloth, or of an elastomerized material. In any case, the ponytail ring 202 forms a complete circle (ring) that will receive and may (or may not) retain the user's ponytail. This will overcome the problem of determining whether to dispose the headband above or below the ponytail, since the ponytail ring allows the headband to intersect the ponytail.

As illustrated in FIG. 2, the ponytail-receiving element 202 is free to rotate within the loops (108, 110) in the ends (104, 106) of the headband element 102, since it is not fixed (e.g., stitched) thereto but rather is simply received by the loops.

Figure 2A:
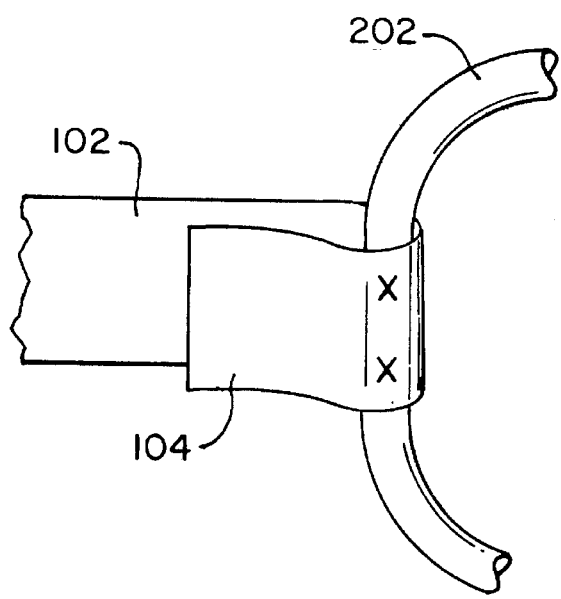
FIG. 2a is a partial perspective view of a rear portion of a headband component, in conjunction with a portion of a ponytail ring component, according to an alternate embodiment of the present invention.

As shown in FIG. 2a, the ponytail-receiving element 202 may alternatively be stitched to the looped ends of the headband element (as indicated by the symbols "x"), so that the ponytail-receiving element is not free to rotate within the loops (108, 110). This figure shows, for example, the assembly of the left half of the ponytail-receiving ring to the left headband end 104. In this case, prior to stitching the ponytail-receiving element to the headband element, the looped ends (108, 110) would be positioned at diametrically-opposed positions on the ponytail-receiving element.

Figure 2B:
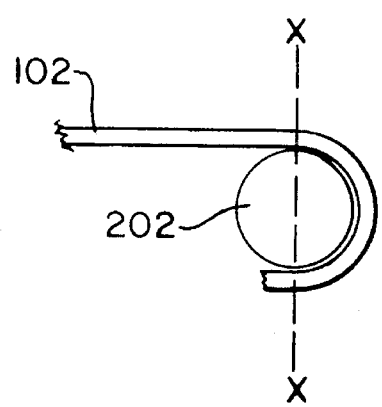
FIG. 2b is a partial cross-sectional view of the headband component and ponytail component, according to an alternate embodiment of the present invention.

FIG. 2b is a cross-sectional view of a portion (e.g., left-hand portion, similar to FIG. 2a) of a headband 102. In FIG. 2b the free ends (one shown) of the headband component are not entirely looped back onto the headband component. Rather, the free ends are inserted completely through the inside of the ponytail ring, then stitched through opposed exterior surfaces of the ponytail ring (as indicated by the dashed line with "x" at each end). In this regard, the free ends are partially looped.

Each alternative of allowing the ponytail ring to rotate (e.g., FIG. 2) or not allowing the ponytail ring to rotate (e.g., FIG. 2a), or not looping the ends of the headband component (e.g., FIG. 2b) has its own benefits and advantages.

As is evident from the figures described hereinabove, the basic headband of the present invention comprises:

- a flat headband element having two ends, each of which is formed into a loop;
    - optionally, forming the headband element as a folded piece of material;
        - optionally stitching the edges of the folded material to form a tubular headband element;
        - optionally providing an elastic strip within the tubular headband element;
- a circular ponytail-receiving element (ring) disposed within the two looped ends of the headband element;
    - optionally stitching the ponytail-receiving element to the looped ends of the headband element;
    - optionally, forming the ponytail-receiving element as a folded piece of material;
        - optionally stitching the edges of the folded material to form a tubular headband element;
        - optionally providing an elastic strip within the tubular ponytail-receiving element.

Generally, the headband element forms a segment of a circle (the two ends are not joined to one another) having a first axis, and the ponytail-receiving element forms a complete circle having a second axis, and the second axis is at a right angle to the first axis.

BRAIDED HEADBAND ELEMENT

In this embodiment, the headband element is formed as a braid, having a plurality of strands. Three or more strands is preferred. Generally, the figures showing braided embodiments are exploded, to better see the individual strands of the braids.

Figure 3:
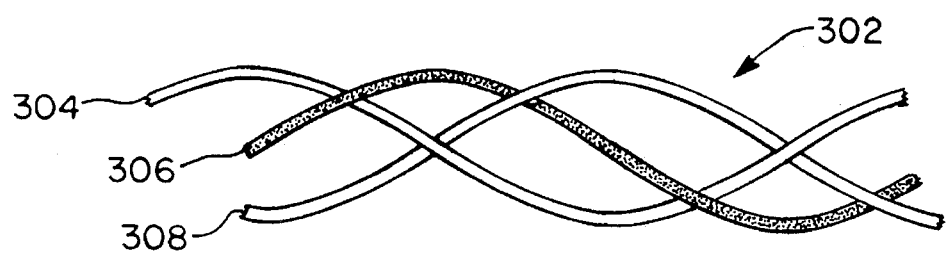
FIG. 3 is an exploded view of a portion of a braided headband component having three strands, according to the present invention.

FIG. 3 shows a headband element 302 formed with three strands 304, 306, 308. The strand 306 is shown colored in, for illustrative clarity.

Each strand can be formed of a single thickness of material, or can be formed of a folded-over strip of material having aligned edges, in the manner previously shown in FIG. 1a. The width of each strand is approximately ½–¾" (if folded over, twice that before folding over). Each folded-over strand can have its aligned edges secured to one another, in the manner previously shown in FIGS. 1c and 1d, to form elongated tubes. Furthermore, an elastic strip can be disposed in each of the folded-over, aligned edge secured strands, in the manner shown in FIGS. 1c and 1d. Preferably, each strand is formed according to the techniques shown in FIG. 1b, as a multi-folded strand.

Although not explicitly illustrated in FIG. 3, the ends of the braided headband element can be looped in the manner illustrated in FIG. 1, for receiving, within the end loops, the ponytail-receiving element (ring). Two functions can be achieved at once—namely, by looping the ends back onto the body of the headband, and securing the ends to the body of the headband, the end loops can be formed as well as securing the braided strands from unraveling (un-braiding) themselves.

It should be understood that the illustration of FIG. 3 shows the strands rather loosely braided ("exploded view"), with voids between the respective strands. This has been done solely for the purpose of illustrative clarity. In practice, the strands would be more tightly braided, so that the headband element resembles a flat band without voids between the individual strands.

An advantage of a braided construction is that it is inherently resilient. In other words, even though individual strands may be formed of a material that is not particularly resilient, the overall braided construction will be longitudinally yielding (resilient), so that a one size (length) of headband will fit snugly about various size heads. By using a braided construction for the headband element, it is not necessary to include elastic strips. Strands formed of strips of folded over, absorbent cloth material will suffice (without binding the aligned edges).

Figure 3A:
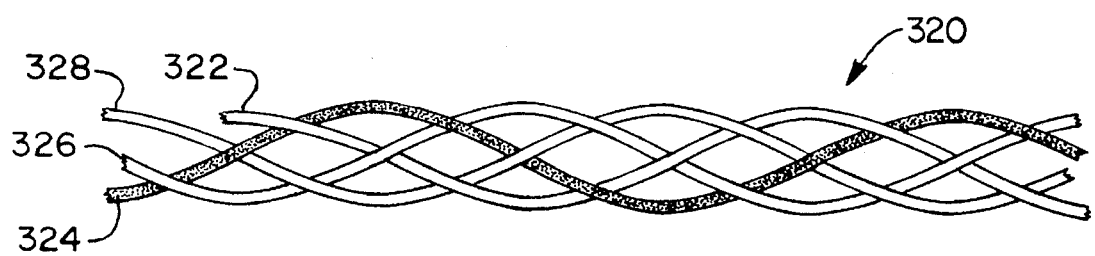
FIG. 3a is an exploded view of a portion of a braided headband component having four strands, according to the present invention.

FIG. 3a shows a headband element 320 formed with four individual strands 322, 324, 326 and 328. The strand 324 is shown colored in, for illustrative clarity.

As in the FIG. 3 embodiment (3-strand, braided headband element), each strand can be formed of a single thickness of material, or can be formed of a folded-over strip of material having aligned edges, in the manner previously shown in FIG. 1a. The width of each strand is approximately ½–¾" (if folded over, twice that before folding over). Each folded-over strand can have its aligned edges secured to one another, in the manner previously shown in FIG. 1c and 1d, to form elongated tubes. Furthermore, an elastic strip can be disposed in each of the folded-over, aligned edge secured strands, in the manner shown in FIGS. 1c and 1d. Furthermore, the elongated tube can be inverted prior to inserting the elastic strip, in the manner shown in FIG. 1d. Preferably, each strand is formed according to the techniques shown in FIG. 1b, as a multi-folded strand.

Although not explicitly illustrated in FIG. 3a, the ends of the braided headband element 320 can be looped in the manner illustrated in FIG. 1, for receiving, within the end loops, the ponytail-receiving element (ring). Two functions can be achieved at once—namely, by looping the ends back onto the body of the headband, and securing the ends to the body of the headband, the end loops can be formed as well as securing the braided strands from unraveling (un-braiding) themselves.

It should be understood that the illustration of FIG. 3a shows the strands rather loosely braided ("exploded view"), with voids between the respective strands. This has been done solely for the purpose of illustrative clarity. In practice, the strands would be more tightly braided, so that the headband element resembles a flat band without voids between the individual strands.

Again, an advantage of a braided construction is that it is inherently resilient. In other words, even though the individual strands may be formed of a material that is not particularly resilient, the overall braided construction will be longitudinally yielding (resilient), so that a one size (length) of headband will fit snugly about various size heads. By using a braided construction for the headband element, it is not necessary to include elastic strips. Strands formed of strips of folded over, absorbent cloth material will suffice (without binding the aligned edges).

Figure 3B:
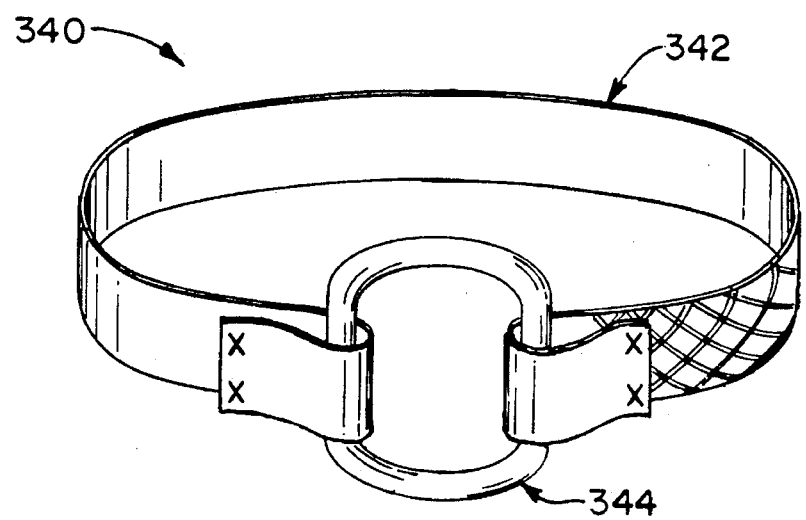
FIG. 3b is a perspective view of a braided headband component, in conjunction with a ponytail ring component, according to the present invention. (Only a portion of the headband component is shown braided, for illustrative clarity.)

FIG. 3b shows a complete headband assembly 340, comprising a braided headband element 342 (comparable to the braided headband elements 302 or 320, previously discussed), having its ends looped over and sewn ("x"), in a manner similar to the illustration of FIG. 2. In this figure, a ponytail-receiving ring 344 is shown received, but free to rotate, within the end loops, in a manner similar to what was shown with respect to FIG. 2. The ponytail-receiving ring can also be sewn into the end loops, at diametrically-opposed positions on the ring, in a manner similar to what was shown with respect to FIGS. 2a and 2b.

Using a 4-strand braided headband element, or other multi-strand embodiment, preferably using an even number of strands, it is possible to manufacture the headband element and the ponytail-receiving element as a single unit, rather than as two separate elements.

Figure 4:
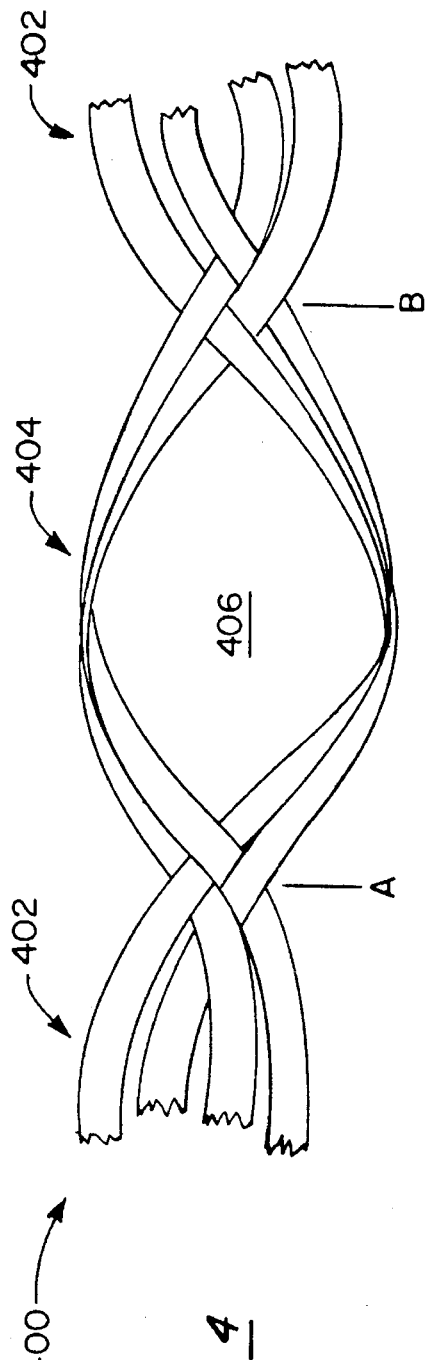
FIG. 4 is a perspective view of a braided headband with a unitary ponytail-receiving element, according to the present invention.

FIG. 4 shows a embodiment of a single-unit headband 400 comprising a headband portion 402 and a ponytail-receiving portion 404. The entire headband is formed of a braid having four strands At two positions "A" and "B" wherebetween it is desired to form the ponytail-receiving portion 404 (these two positions corresponding to the ends of a separate headband component, such as is shown in FIG. 3b), the four strands are separated into two groups of two strands each, so that there is, in essence, an opening 406 created for receiving a person's ponytail. In order that the ponytail-receiving opening remains in place, it is preferable to sew the strands of the band 402 at the positions "A" and "B". (The stitching is omitted from this view.)

PREFERRED EMBODIMENTS

Various preferred embodiments, as presently contemplated by the inventors, is now described, without prejudice or limitation.

Figure 5:
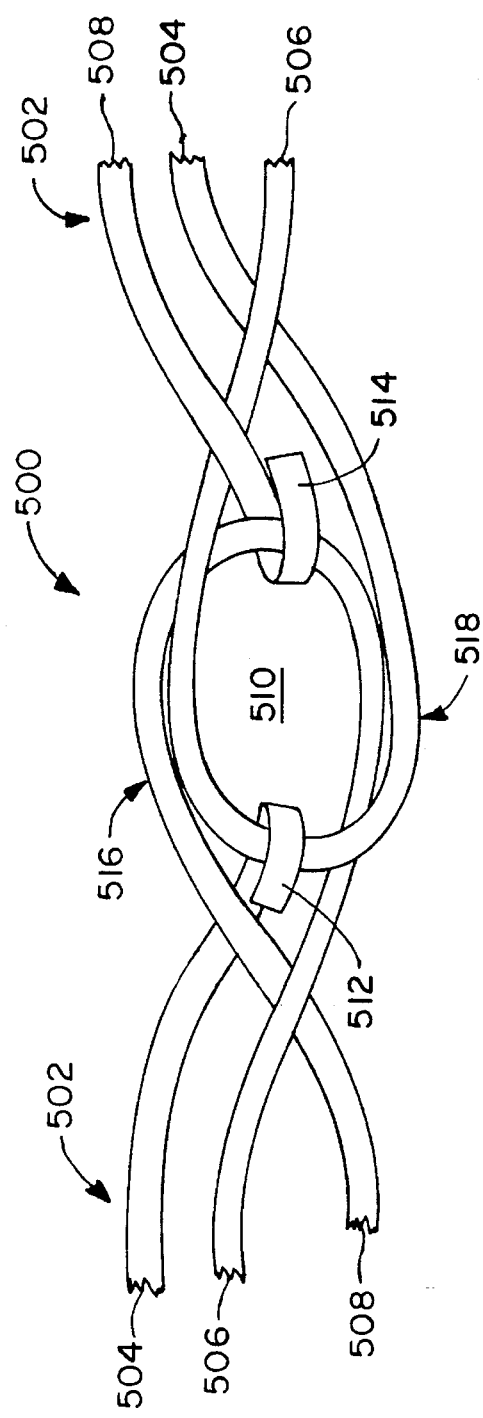
FIG. 5 shows, schematically, the construction of a braided headband with integral ponytail-receiving ring, according to an embodiment of the invention.

FIG. 5 shows an embodiment of a braided headband with integral ponytail-receiving ring. Generally, this embodiment of a headband 500 employs a 3-strand braid (see, e.g., FIG. 3), and incorporates the ponytail-receiving component into the structure of the braid itself.

As shown in FIG. 5, a head-encircling portion 502 (similar to the band 302) is formed of a three-strand braid.

The three strands 504, 506, 508 of the headband portion 502 approach both sides of a predetermined location 510 whereat a ponytail-receiving opening 510 (compare 406, FIG. 4) is to be formed.

It should be understood that the same strand (e.g., 504) may not be on the top (as viewed in the figure) of the braid on both sides of the ponytail-receiving opening 510. Or it may. In this figure, it is illustrated that the strand 504 is atop the braid on the left (as viewed) of the ponytail-receiving opening, and the braid 508 is atop the braid on the right (as viewed) of the ponytail-receiving opening.

With reference to the left side of the ponytail-receiving opening 510, a selected one (504) of the strands is cut, and its free end is looped back onto the headband portion, and stitched thereto. (The stitching of the looped-back free end is omitted from the figure, for illustrative clarity. Generally, in this figure, the strands are shown much thinner than they would be in actual practice, as well as being separated from one another for illustrative clarity). In other words, the selected strand is stitched onto itself, as well as onto the other two of the strands (506, 508). This results in a loop 512 being formed of a single one (504) of three strands (504, 506, 508), which is functionally analogous to the loop 108 shown in FIG. 1.

With reference to the right side of the ponytail-receiving location, a selected one (508) of the strands is cut, and its end is looped back onto the headband portion, and stitched thereto. (Again, the stitching is omitted from the figure.) In other words, the selected strand (508) is stitched onto itself, as well as onto the other two of the strands (504, 506). This results in a loop 514 being formed of a single strand (508), which is functionally analogous to the loop 110 shown in FIG. 1.

Two loops 512 and 514 are thus formed, each at a "virtual" (as opposed to actual) end of the headband portion.

From left-to-right (as viewed in the figure), the strands 506 and 508, which have been stitched to the looped-back end of the strand 504, continue approximately two inches past the left loop 512, are cut, and their ends are joined (stitched) to one another, forming a portion 516 of a ring for receiving a ponytail. This ring portion 516 passes within the loop 514, preferably without being stitched thereto. Preferably, the ends of the strands 506, 508 are stitched to one another at a position which is concealed by the loop 516. In essence, at the left hand side of the ponytail-receiving opening 510, the strand 506 "becomes" the strand 508, after passing through the right hand loop 514.

From right-to-left (as viewed in the figure), the strands 504 and 506, which have been stitched to the looped-back end of the strand 508, continue approximately two inches past the loop 514, are cut, and their ends are joined (stitched) to one another, forming another portion 518 of the ring for receiving a ponytail. This ring portion 518 passes within the loop 512, preferably without being stitched thereto. Preferably, the ends of the strands 504 and 506 are stitched to one another, at a hidden position within the loop 512. The ring portion 518 formed by the strands 504 and 506 is aligned (coaxially) with the ring portion 516 formed by the strands

506 and 508. These two overlying (or underlying) ring portions 516 and 518 form a ponytail-receiving ring analogous to the ring 202 of FIG. 2.

There has been described a headband 500 having three distinct strands 504, 506 and 508. Each of the strands may be of a different color. Two of the strands are nominally x=30 inches in length. The remaining one of the strands is y=24 inches in length. The ratio of y:x is therefore approximately 1.25:1±10%.

By carefully following the "flow" of the strands 504, 506 and 508, it will be evident that the headband 500 can be made using a single, long, continuous strand, rather than by using three distinct strands (e.g., 504, 506, 508). For example, starting with the free (looped) end of the strand 504 (at the left hand side of the ponytail-receiving opening), proceeding to the left (off the page), reentering the page at the right, following the strand 504 around the ponytail-receiving ring portion 518, it is seen that the strand 504 "becomes" the strand 506. Following the strand 506 back off the page (to the right), reentering the page from the left, it is seen that the strand 506 "becomes" the strand 508 within the loop 514. Following the strand 508 back to the left, and re-entering the page from the right, it is seen that the strand 508 has a free end looped to form the loop 514. Hence, a three-strand, braided headband, with an integral ponytail-receiving portion, can be formed of a single, long strand of material. (Hence, the and joining of the "ends" of the strands 506 and 508, to form the ring portion 516, as well as the joining of the "ends" of the strands 504 and 506 to form the ring portion 518, as described hereinabove, becomes unnecessary.) Such a long strand, used to form a braided headband, would be approximately three times longer than the circumference of the finished headband.

A single long continuous strand can also be used to make a braided headband with integral ponytail-receiving ring in a different manner.

Figure 5A:
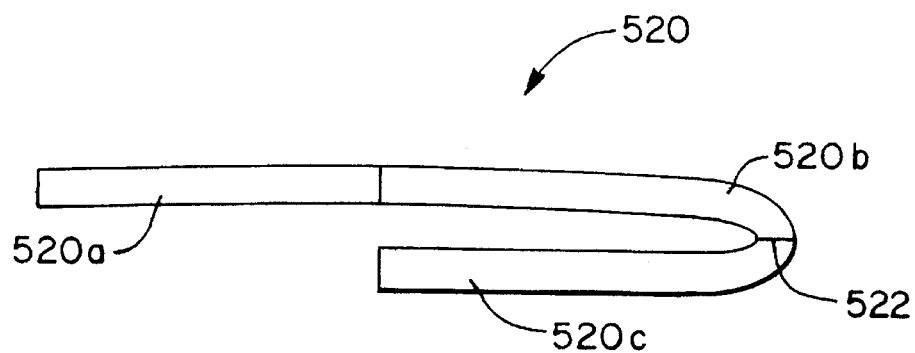
FIGS. 5a and 5b show, schematically, the construction of a braided headband with integral ponytail-receiving ring, according to an alternate embodiment of the invention.
Figure 5B:
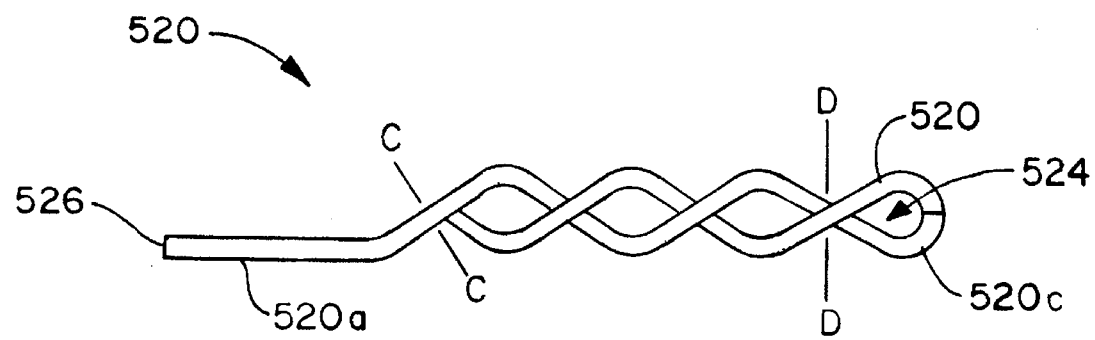

FIGS. 5a and 5b show another preferred embodiment of a braided headband with integral ponytail-receiving ring.

FIG. 5a shows a single long continuous strand 520 having three segments 520a, 520b and 520c. The long strand 520 can be made of three pieces of different colored material (e.g., red, white and blue), if preferred, stitched end-to-end.

As shown in FIG. 5a, the strand 520 is folded back onto itself at a position approximately one-third the distance from an end. This position is indicated as 522, this conveniently being the seam between the two pieces 520b and 520c (if the long strand is made of sewn-together pieces).

As shown in FIG. 5b, the segments 520b and 520c are then partially braided (twisted). This results in a ring 524, similar to one of the aforementioned ring portions 516 or 518 (FIG. 5), which will be a ponytail-receiving ring.

One segment 520a extends beyond the partially-braided segment, and has a free end 526. The free end 526 can be passed through the ring 524, and drawn nearly fully through the ring 524 so that a position C—C of the strand 520a loops around and retains the right side (as viewed) of the ring 524. Then, the free end 526 of the segment 520a can be threaded through the partial braid formed by the segments 520b and 520c, to complete a three-strand braid. The end 526 of the segment 520a can simply be sewn to the first cross-over of the strands 520b and 520c, at a position indicated as D—D, or it can first be inserted through and around the left side (as viewed) of the loop 524 prior to sewing to the strands 520b and 520c, to maintain symmetry about the loop 524. In the latter case, the resulting headband would resemble the headband 500, except that there is only a single-strand ponytail-receiving ring formed rather than a double strand ponytail-receiving ring (as in FIG. 5). Such a procedure results in somewhat less bulk adjacent the ponytail-receiving ring than in the headband 500.

The completed headband 520 will resemble the completed headband 500 (FIG. 5), except that the ponytail-receiving ring is single (one strand) instead of double.

FIGS. 5c and 5d show yet another preferred embodiment of a braided headband with integral ponytail-receiving ring.

In this embodiment of the invention, shown in FIGS. 5c and 5d, two strands are used to form a braided headband 540. One of the strands is nominally twice the length of the other. For example, a strand 542 may be 48 inches long, and a strand 544 may be 24" long. In a manner similar to the headband 520, the strand 542 has two nominally equal-length segments 542a and 542b (e.g., each segment is nominally 24 inches long), which may be discrete pieces sewn together, as indicated by the line 546. For purposes of describing this embodiment, it is assumed that two pieces are sewn together, end-to-end, to form the segments 542a and 542b. Further, for clarity of illustration, the segment 542a is illustrated as being formed of a blue ("B") material, and the segment 542b is illustrated as being formed of a white ("W") material. The segment 544, shown in FIG. 5d is shown with shading lines, and is illustrated as being formed of a red ("R") material.

As shown in FIG. 5c, the first step in making this embodiment is to partially braid the segments 542a and 542b, in a manner similar to the partial braiding of the segments 520b and 520c (FIG. 5b), so that there is a ponytail-receiving ring 548 located approximately halfway between the free ends of the segments 542a and 542b. The resulting partial braid (twisted segments) is preferably relatively flat. In this, and in other embodiments employing flat strands, the resulting braid is preferably caused to be relatively flat (e.g., nearly two-dimensional).

As shown in FIG. 5c, the free end 550 of one of the segments 542a is permitted (caused) to extend further than the free end 552 of the other segment 542b, by a distance of approximately one inch.

The third (red) strand 544 is threaded through the partial braid formed by the segments 542a dn 542b, in the manner shown in FIG. 5d, so as to have one free end 554 passing through the ring 548. The other free end 556 of the (red) strand 544 is terminated at the same position as the free end 552 of the segment 542b.

The end 554 can now be looped, through the left side (as viewed) of the ring 548, back onto the body of the headband, and stitched to the segments 542a and 542b, as indicated at E—E. This is similar to the end 512 being looped around the ring portion 518 (FIG. 5).

The end 550 of the segment 542a can now be looped, through the right side (as viewed) of the ring 548, back onto the body of the headband, and stitched to the segments 542a and 542b, as indicated at F–F. This is similar to the end 512 being looped around the ring portion 516 (FIG. 5).

The completed headband 540 will resemble the completed headband 500 (FIG. 5), except that the ponytail-receiving ring is single (one strand) instead of double.

The construction shown in FIGS. 5c and 5d is the most preferred construction contemplated by the inventors at the time of making this invention.

VISOR ELEMENT

As mentioned hereinabove, a visor will shield the person's eyes from the sun. According to an aspect of the invention, a visor element (component) can be added to the headband.

Figure 6:
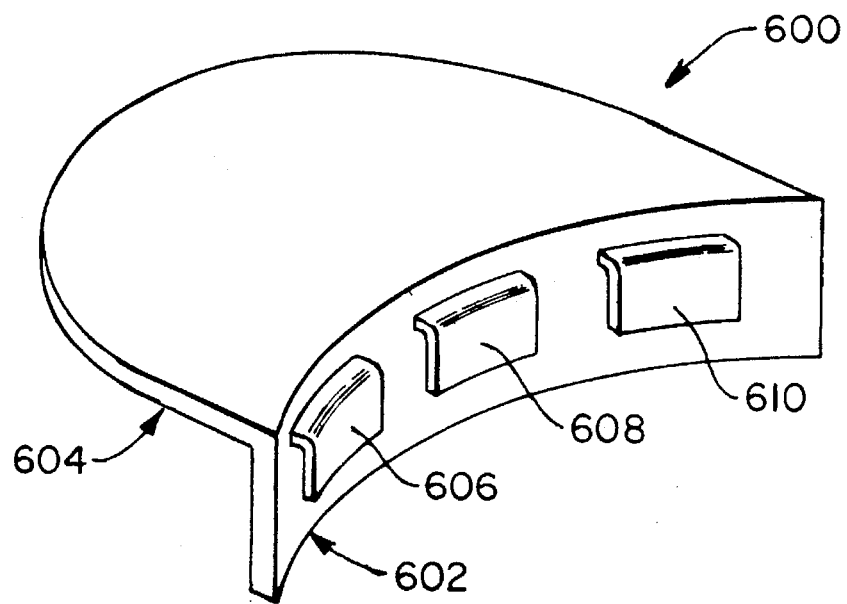
FIG. 6 is a perspective view showing a visor element for use with a headband, according to the present invention.

FIG. 6 shows an embodiment of a visor element 600 for use with any headband, such as the various headbands described hereinabove.

The visor 600 is suitably formed of a rigid, preferably opaque (e.g., to sunlight) material, such as plastic, and is provided with means for securing the visor element to a front portion (above the person's eyes) of a headband.

The visor 600 is preferably formed as a single, molded plastic component, having:

an arcuate base portion 602, sized and contoured to extend as a band circumferentially around a person's forehead, and a "bill" portion 604, sized to extend from the person's forehead above their eyes.

The base portion 602 is generally in the form of an arcuate band, 1–2 inches tall, and 6–9 inches in circumferential extent.

The bill portion 604 is generally in the form of a semicircle, with its flat side supported by an outside surface (away from the person's head, in use) of the band portion, and having a radius of 3–6 inches.

The means for securing the visor element 600 to the front portion of a headband component is disposed, in this embodiment, on the inside surface (towards the person's head, in use) of the base portion 602, and suitably comprises three tabs 606, 608 and 610. One tab 608 is disposed approximately midway along the base portion, and extends from near the bottom edge of the base portion towards the top edge of the base portion. The other two tabs 606 and 6104 are disposed on either side of the central tab 608, towards the ends of the base portion, and extend from near the top edge of the base portion towards the bottom edge of the base portion. (Top and bottom are as viewed in the figure, and vis-a-vis the tabs, could be transposed, one-for-another—the relevant feature being that the tabs alternate from top to bottom edge.) In this manner, the visor may be secured to the front portion of a relatively flat headband, so that the user's eyes are shielded from the sun.

In an alternate construction of the visor, the tabs could be disposed on an external, rather than internal, surface of the base portion (602). This is somewhat preferred, in that a flat surface (i.e., of the base portion) would be against the person's forehead, rather than the tabs. (The tabs being against the person's forehead could result in some degree of discomfort.)

Also, the bill portion 604 could extend from the bottom edge of the base portion 602, rather than from the top edge. Extending the bill portion from the bottom edge of the base portion would dispose the bill portion closer to the user's eyes, and is preferred.

Figure 6B:
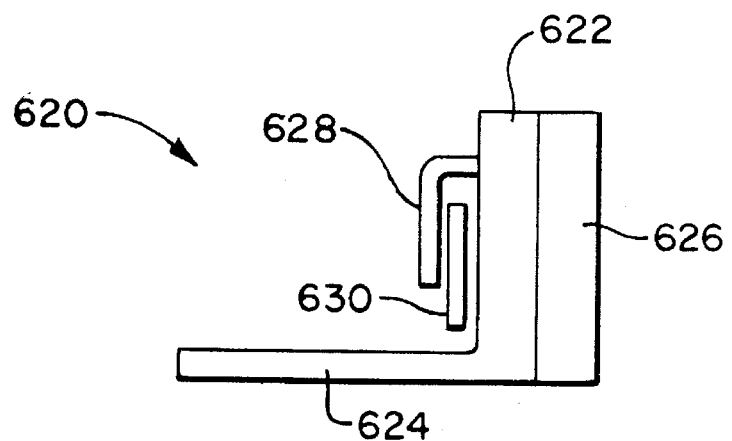
FIG. 6a is a near-sighted cross-sectional view of an alternate embodiment of a visor element for use with a headband, according to the present invention.

FIG. 6b shows a preferred embodiment of a visor 620, suitable for attaching to a headband, such as any of the headbands described hereinabove.

The visor 620 has a base portion 622, which is suitably similar to the base portion 602 (FIG. 6), and has a bill portion 624 similar to the bill portion 604 (FIG. 6). In this case, the bill portion 624 is shown extending from the bottom edge of the base portion 622.

On the inside surface (towards the user's forehead) of the base portion 622, there is disposed a strip of absorbent material, such as terrycloth, or any of the other cloth materials described hereinabove. This provides a comfortable cushion for the user wearing the visor 620.

Any suitable means may be employed to secure the visor element to a headband. In this illustration, a tab 628 (similar to any of the tabs 606, 608, 610, described hereinabove with respect to FIG. 6) is shown disposed on an exterior surface of the base portion. Also illustrated is a headband 630 extending through the tab. (This figure is a "near-sighted" cross-section, so only one tab is visible.)

In use, the headband of the present invention provides a useful method of absorbing perspiration from a persons head, holding the person's hair away from their eyes, and receiving the person's ponytail.

Generally, especially in the braided constructions formed of strands (e.g., folded-over strands), without elastic, the ponytail-receiving ring does not retain a person's ponytail, per se. To do would require requires an aggressive elastic. It is generally intended that a person first form their ponytail, with an elastic which is not part of the present invention, then simply insert their ponytail through the ponytail-retaining ring. Actually, the ponytail-receiving simply provides a convenience for locating the headband on the user's head, by allowing the person's ponytail to pass therethrough. Any "grabbing" of the ponytail itself by the ponytail-receiving ring would therefore be considered incidental.

In the braided construction, the user is simply required to fit the headband to their head, and insert their ponytail through the ponytail-receiving opening. Further, a visor element may be removably fitted to the headband.

The above, and other objects, features, advantages and embodiments of the invention, including other (i.e., additional) embodiments of the techniques discussed above may become apparent to one having ordinary skill in the art to which this invention most nearly pertains, and such other and additional embodiments are deemed to be within the spirit and scope of the present invention.

What is claimed is:

1. A braided headband, comprising:

two strands of material, a one relatively long strand and another relatively short strand;

the relatively long strand is doubled back onto itself and partially braided, a ponytail-receiving ring being formed at a midpoint of the relatively long strand, a one end of the relatively long strand extending beyond an other end of the relatively long strand;

the relatively short strand is threaded through the partially-braided relatively long strand;

a one end of the relatively short strand extending through a one side of the ponytail-receiving ring and looped back onto the partially-braided relatively long strand; and the one end of the relatively long strand extending through an other side of the ponytail-receiving ring and looped back onto the partially-braided relatively long strand.

2. The braided headband, according to claim 1, wherein:

the relatively long strand is formed as a folded piece of material having at least one fold and two aligned edges.

3. The braided headband according to claim 1, wherein:

the strands form a circle having a first axis;

the ponytail-receiving ring forms a circle having a second axis; and the second axis is at a right angle to the first axis.

4. The braided headband, according to claim 1, further comprising:

a visor element fittable to the strands.

5. A braided headband, according to claim 19, wherein:

the relatively-long strand is formed of two strands linked end-to-end.

6. The braided headband, according to claim 1 wherein:

the relatively short strand is formed as a folded piece of material having at least one fold and two aligned edges.

* * * * *